(12) United States Patent
Horvath et al.

(10) Patent No.: US 10,987,473 B2
(45) Date of Patent: Apr. 27, 2021

(54) LUBRICATED PEN NEEDLE

(75) Inventors: Joshua Horvath, Sparta, NJ (US);
Edward Rosen, Morristown, NJ (US);
Paul Upham, Jersey City, NJ (US)

(73) Assignee: Becton, Dickinson and Company,
Franklin Lakes, NJ (US)

(*) Notice: Subject to any disclaimer, the term of this patent is extended or adjusted under 35 U.S.C. 154(b) by 0 days.

(21) Appl. No.: 13/138,305

(22) PCT Filed: Feb. 4, 2010

(86) PCT No.: PCT/US2010/000319
§ 371 (c)(1),
(2), (4) Date: Oct. 11, 2011

(87) PCT Pub. No.: WO2010/090747
PCT Pub. Date: Aug. 12, 2010

(65) Prior Publication Data
US 2012/0029469 A1 Feb. 2, 2012

Related U.S. Application Data (60) Provisional application No. 61/150,677, filed on Feb. 6, 2009.

(51) Int. Cl.
*A61M 5/32* (2006.01)
*A61M 5/34* (2006.01)
*A61M 5/00* (2006.01)

(52) U.S. Cl.
CPC ............ *A61M 5/3202* (2013.01); *A61M 5/32* (2013.01); *A61M 5/3213* (2013.01); *A61M 5/002* (2013.01);
(Continued)

(58) Field of Classification Search
CPC ... A61M 5/3202; A61M 5/002; A61M 5/3213
(Continued)

(56) References Cited

U.S. PATENT DOCUMENTS 2,400,722 A * 5/1946 Swan .................... A61M 5/001
206/210
3,270,743 A 9/1966 Gingras
(Continued)

FOREIGN PATENT DOCUMENTS

EP 0 615 768 9/1994
FR 2 571 972 4/1986
(Continued)

OTHER PUBLICATIONS

Kohn et al., Guidelines for Infection Control in Dental Health-Care Settings—2003, Dec. 9, 2003, The Center for Disease Control and Prevention.*
(Continued)

*Primary Examiner* — William R Carpenter
(74) *Attorney, Agent, or Firm* — Dickinson Wright PLLC (57) ABSTRACT

A pen needle (531) includes a hub (511) and a needle (513) fixedly connected to the hub (511). An outer cover (501) receives the hub (511). A lubricant reservoir (503) is disposed in the outer cover (501) such that a portion of the needle (513) is disposed in the lubricant reservoir (503) when the hub (511) is received by the outer cover (501). Lubrication of the needle (513) facilitates multiple injections.

22 Claims, 9 Drawing Sheets

(52) U.S. Cl.
CPC ............. *A61M 5/329* (2013.01); *A61M 5/347* (2013.01); *A61M 2205/0222* (2013.01)

(58) Field of Classification Search
USPC ................ 128/919; 206/363, 364, 365, 366; 604/506, 171, 172, 192, 198, 199, 263, 604/265, 272
See application file for complete search history.

(56) References Cited

U.S. PATENT DOCUMENTS

| | | | | |
|---|---|---|---|---|
| 4,085,737 A | * | 4/1978 | Bordow | A61B 5/15003 600/576 |
| 4,248,246 A | * | 2/1981 | Ikeda | A61B 10/00 600/578 |
| 4,435,177 A | * | 3/1984 | Kuhlemann | A61J 1/1487 604/199 |
| 4,474,734 A | * | 10/1984 | Cooper | A61L 2/07 422/31 |
| 4,623,329 A | | 11/1986 | Drobish | |
| 5,084,027 A | * | 1/1992 | Bernard | A61M 5/3213 206/365 |
| 5,147,309 A | * | 9/1992 | Hemmerich | A61M 5/002 604/122 |
| 5,226,896 A | * | 7/1993 | Harris | A61M 5/31551 604/211 |
| 5,545,143 A | * | 8/1996 | Fischell | A61M 5/158 604/180 |
| 5,567,495 A | | 10/1996 | Modak | |
| 5,785,688 A | | 7/1998 | Joshi | |
| 5,911,711 A | | 6/1999 | Pelkey | |
| 5,941,857 A | | 8/1999 | Nguyen | |
| 5,968,021 A | * | 10/1999 | Ejlersen | A61M 5/3213 206/365 |
| 5,971,966 A | * | 10/1999 | Lav | A61M 5/002 206/365 |
| 5,980,495 A | * | 11/1999 | Heinz | A61M 5/3202 128/919 |
| 6,001,089 A | * | 12/1999 | Burroughs | A61M 5/31551 604/208 |
| 6,017,328 A | | 1/2000 | Fischell | |
| 6,458,867 B1 | * | 10/2002 | Wang | A61L 29/085 523/105 |
| 6,485,474 B1 | * | 11/2002 | Heinz | A61M 5/3202 128/919 |
| 6,726,649 B2 | * | 4/2004 | Swenson | A61B 17/205 206/365 |
| 6,880,701 B2 | * | 4/2005 | Bergeron | A61M 5/3205 206/365 |
| 2001/0001443 A1 | * | 5/2001 | Kayerod | A61M 25/002 206/364 |
| 2002/0066686 A1 | * | 6/2002 | Montenieri | A61M 5/3205 206/365 |
| 2002/0103461 A1 | * | 8/2002 | Asbaghi | A61M 5/326 604/198 |
| 2006/0032769 A1 | * | 2/2006 | Erickson | A61M 5/002 206/365 |
| 2006/0184117 A1 | * | 8/2006 | Knight | A61M 5/24 604/135 |
| 2006/0196783 A1 | * | 9/2006 | Bruun | A61M 25/002 206/210 |
| 2006/0229562 A1 | | 10/2006 | Marsh et al. | |
| 2007/0049870 A1 | | 3/2007 | Gray | |
| 2007/0149924 A1 | | 6/2007 | Marsh | |
| 2009/0069752 A1 | * | 3/2009 | Raj | A61M 5/3202 604/192 |

FOREIGN PATENT DOCUMENTS

| | | |
|---|---|---|
| GB | 2 232 601 | 12/1990 |
| JP | 6733 | 9/1907 |
| JP | 3-129152 | 12/1991 |
| JP | 4-90353 | 8/1992 |
| JP | 09-124511 | 5/1997 |
| JP | 2000-024108 | 1/2000 |
| JP | 2001-500414 A | 1/2001 |
| JP | 2003-079727 A | 3/2003 |
| WO | WO 9311814 A1 * | 6/1993 .......... A61M 5/3213 |

OTHER PUBLICATIONS

Oli et al., Multiple Use of Ordinary Disposable Syringes for Insulin Injections, Jan. 23, 1982, The British Medical Journal, vol. 284, p. 236.*

Sawyer et al., Preventing Needle Stick Injuries and the Use of Dental Safety Syringes, Oct. 2010, Worksafe BC, p. 1-53.*

Extended European Search Report issued in Application No. 10738863.9-2320 dated Nov. 16, 2012.

Office Action dated Nov. 26, 2013 in Japanese Patent Application No. 2011-549160.

* cited by examiner

LUBRICATED PEN NEEDLE

CROSS REFERENCE TO RELATED APPLICATION

This application is the national stage under 35 U.S.C. § 371 of International Application No. PCT/US2010/000319, filed Feb. 4, 2010, which claims the benefit under 35 U.S.C. § 119(e) of U.S. Provisional Application Ser. No. 61/150,677, filed Feb. 6, 2009, the entire content of which is hereby incorporated by reference.

FIELD OF THE INVENTION

The present invention relates generally to a lubricated needle for a drug delivery device. More particularly, the present invention relates to a pen needle having a lubricated needle to facilitate multiple injections. Still more particularly, the present invention relates to an outer cover having a lubricant reservoir that lubricates a needle of a pen needle upon placement in the outer cover.

BACKGROUND OF THE INVENTION

Insulin and other injectable medications are commonly given with drug delivery devices, such as a drug delivery pen, whereby a disposable pen needle is attached to facilitate drug container access and allow fluid egress from the container, through the needle and into the patient.

As technology and competition advance, driving the desire for shorter, thinner, less painful, and more efficacious injections, the design of the pen needle and parts thereof becomes more and more important. Designs need to proactively address ergonomically improving injection technique, injection depth control and accuracy, the ability to be safely used and transported to disposal, and protection against misuse while maintaining the ability to be economically manufactured on a mass production scale.

Figure 1:
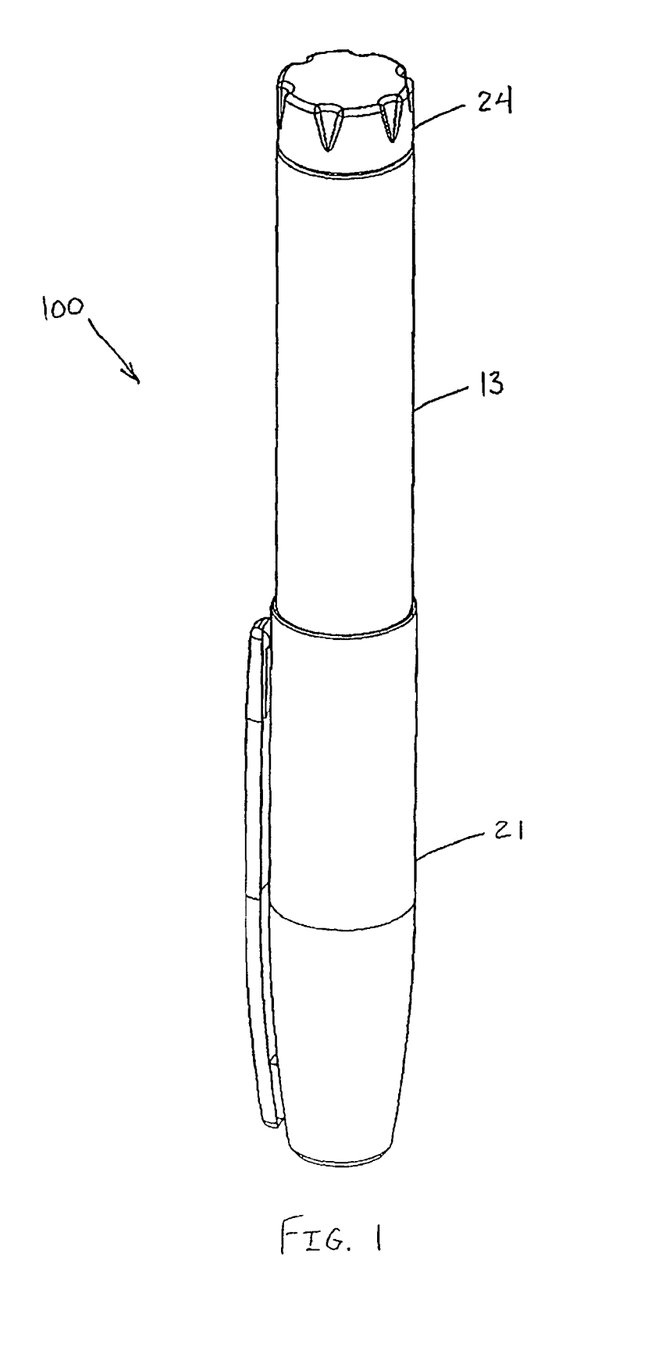
FIG. 1 is a perspective view of an assembled drug delivery pen.
Figure 2:
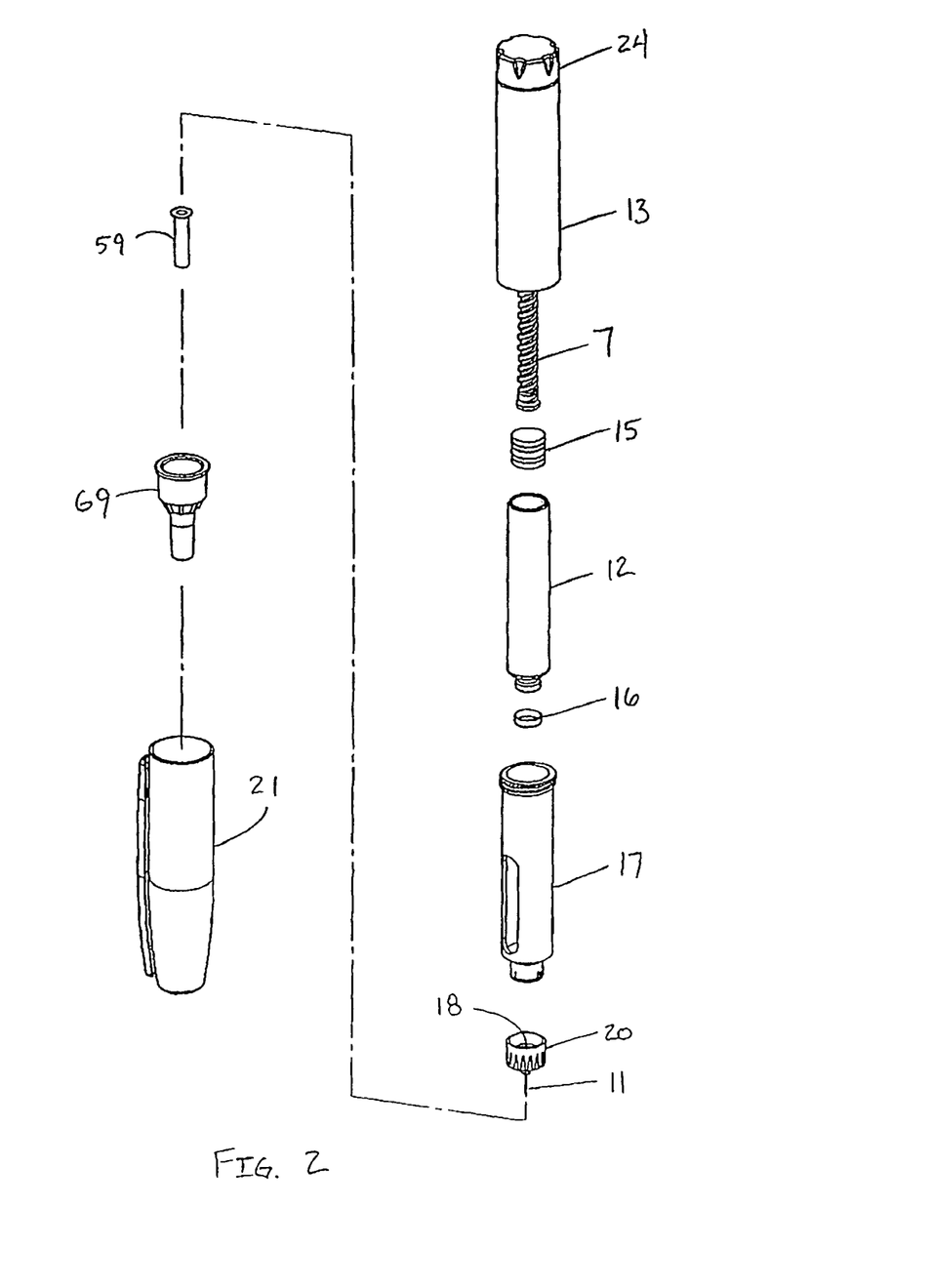
FIG. 2 is an exploded perspective view of the components of the drug delivery pen of FIG. 1.

Drug delivery devices, such as the exemplary drug delivery pen 100 shown in FIGS. 1 and 2, can be designed for subcutaneous, as well as intradermal, injections and typically comprise a dose knob/button 24, an outer sleeve 13, and a cap 21. The dose knob/button 24 allows a user to set the dosage of medication to be injected. The outer sleeve 13 is gripped by the user when injecting medication. The cap 21 is used by the user to securely hold the drug delivery pen 100 in a shirt pocket, purse or other suitable location and provide cover/protection from accidental needle injury.

FIG. 2 is an exploded view of the drug delivery pen 100 of FIG. 1. The dose knob/button 24 has a dual purpose and is used both to set the dosage of the medication to be injected and to inject the dosed medicament via the leadscrew 7 and stopper 15 through the medicament cartridge 12, which is attached to the drug delivery pen through a lower housing 17. In standard drug delivery pens, the dosing and delivery mechanisms are all found within the outer sleeve 13 and are not described in greater detail here as they are understood by those knowledgeable of the prior art. The distal movement of the plunger or stopper 15 within the medicament cartridge 12 causes medication to be forced into the needle 11 of the hub 20. The medicament cartridge 12 is sealed by septum 16, which is punctured by a septum penetrating needle cannula 18 located within the hub 20. The hub 20 is preferably screwed onto the lower housing 17, although other attachment means can be used, such as attaching to the cartridge. To protect a user, or anyone who handles the pen injection device 100, an outer cover 69, which attaches to the hub 20, covers the hub. An inner shield 59 covers the patient needle 11 within the outer cover 69. The inner shield 59 can be secured to the hub 20 to cover the patient needle by any suitable means, such as an interference fit or a snap fit. The outer cover 69 and the inner shield 59 are removed prior to use. The cap 21 fits snugly against outer sleeve 13 to allow a user to securely carry the drug delivery pen 100.

The medicament cartridge 12 is typically a glass tube sealed at one end with the septum 16 and sealed at the other end with the stopper 15. The septum 16 is pierceable by a septum penetrating cannula 18 in the hub 20, but does not move with respect to the medicament cartridge 12. The stopper 15 is axially displaceable within the medicament cartridge 12 while maintaining a fluid tight seal.

Figure 3:
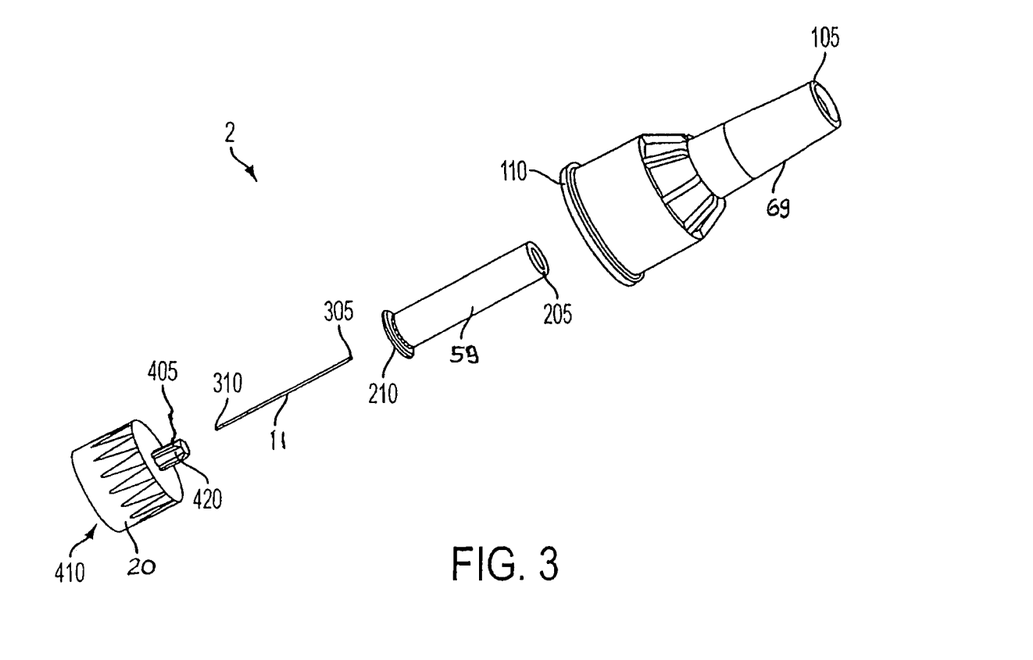
FIG. 3 is an exploded perspective view of the pen needle of the drug delivery pen of FIG. 1.

An exploded perspective view of a pen needle 2 of an exemplary drug delivery pen is shown in FIG. 3. The pen needle 2 includes the cover (outer shield) 69, an inner shield 59, a needle cannula 11, and a hub 20. A proximal end 310 of the needle cannula 11 is inserted into a center opening in the distal (patient) end 405 of the hub 20 until a predetermined length of the distal (patient) end 305 of the needle cannula 11 remains extended. The needle cannula 11 is secured by epoxy or adhesive in the distal end 405 of the hub 20 within the hub protrusion 420.

To protect users from injury and the needle cannula 11 from being damaged, the inner shield 59 covers the exposed portion of the needle cannula 11. The open proximal end 210 of the inner shield 59 is placed over the exposed portion of the needle cannula 11. The open proximal end 110 of the cover 69 envelops the inner shield 59, needle cannula 11, and hub 20.

The distal end 105 of the cover 69 is closed to prevent contamination and damage to the inner components of pen needle 2, and to prevent injury to anyone who may handle it prior to use. The proximal end 410 of the hub 20 is typically covered by a sanitary paper or foil cover (not shown) glued on an end 110 of the cover 69. The drug delivery pen is then ready for shipment to a user. When the user is ready to use the drug delivery pen, the sanitary cover (not shown) is removed from the cover 69, the hub 20 is screwed onto a lower housing 17 of a standard pen 100 (FIGS. 1 and 2), and the cover 69 and shield 59 are separately removed from the hub 20/cannula 11 subassembly by a pulling action. The distal end 205 of the inner shield 59 is closed to cover the distal end 305 of the needle cannula 11 after the cover 69 is removed to protect the user from an accidental needle stick. The inner shield 59 is then removed to access the needle cannula 11. Thus, two separate pulling actions are required to remove both the cover 69 and the shield 59.

Many existing pen needles are used for multiple injections. However, each subsequent injection with the same needle increases the required penetration force, thereby making the injection increasingly difficult and painful. Accordingly, a need exists for facilitating multiple injections with the same needle.

Existing drug delivery pens are disclosed in U.S. Patent Application Publication Nos. 2006/0229562 to Marsh et al., which was published on Oct. 12, 2006, and 2007/0149924 to R. Marsh, which was published on Jun. 28, 2007, the entire contents of both of which are hereby incorporated by reference.

SUMMARY OF THE INVENTION

In accordance with an aspect of the present invention, a lubricated pen needle is provided to facilitate multiple injections.

In accordance with another aspect of the present invention, an outer cover for a pen needle has a lubricant reservoir to lubricate a needle upon disposal therein.

The foregoing objects are basically attained by providing a pen needle having a hub and a needle fixedly connected to the hub. An outer cover receives the hub. A lubricant reservoir is disposed in the outer cover such that a portion of the needle is disposed in the lubricant reservoir when the hub is received by the outer cover.

Objects, advantages, and salient features of the invention will become apparent from the following detailed description, which, taken in conjunction with the annexed drawings, discloses exemplary embodiments of the invention.

BRIEF DESCRIPTION OF THE DRAWINGS

The above benefits and other advantages of the various embodiments of the present invention will be more apparent from the following detailed description of exemplary embodiments of the present invention and from the accompanying drawing figures, in which.

Throughout the drawings, like reference numbers will be understood to refer to like parts, components and structures.

DETAILED DESCRIPTION OF THE EXEMPLARY EMBODIMENTS

The following description and details of exemplary embodiments of the present invention, while generally disclosed in a typical drug delivery pen, as shown in FIGS. 1-3, could more broadly apply to a pen needle for use in conjunction with, or incorporated onto, other injection devices, such as syringes, autoinjectors and infusion devices.

Figure 4:
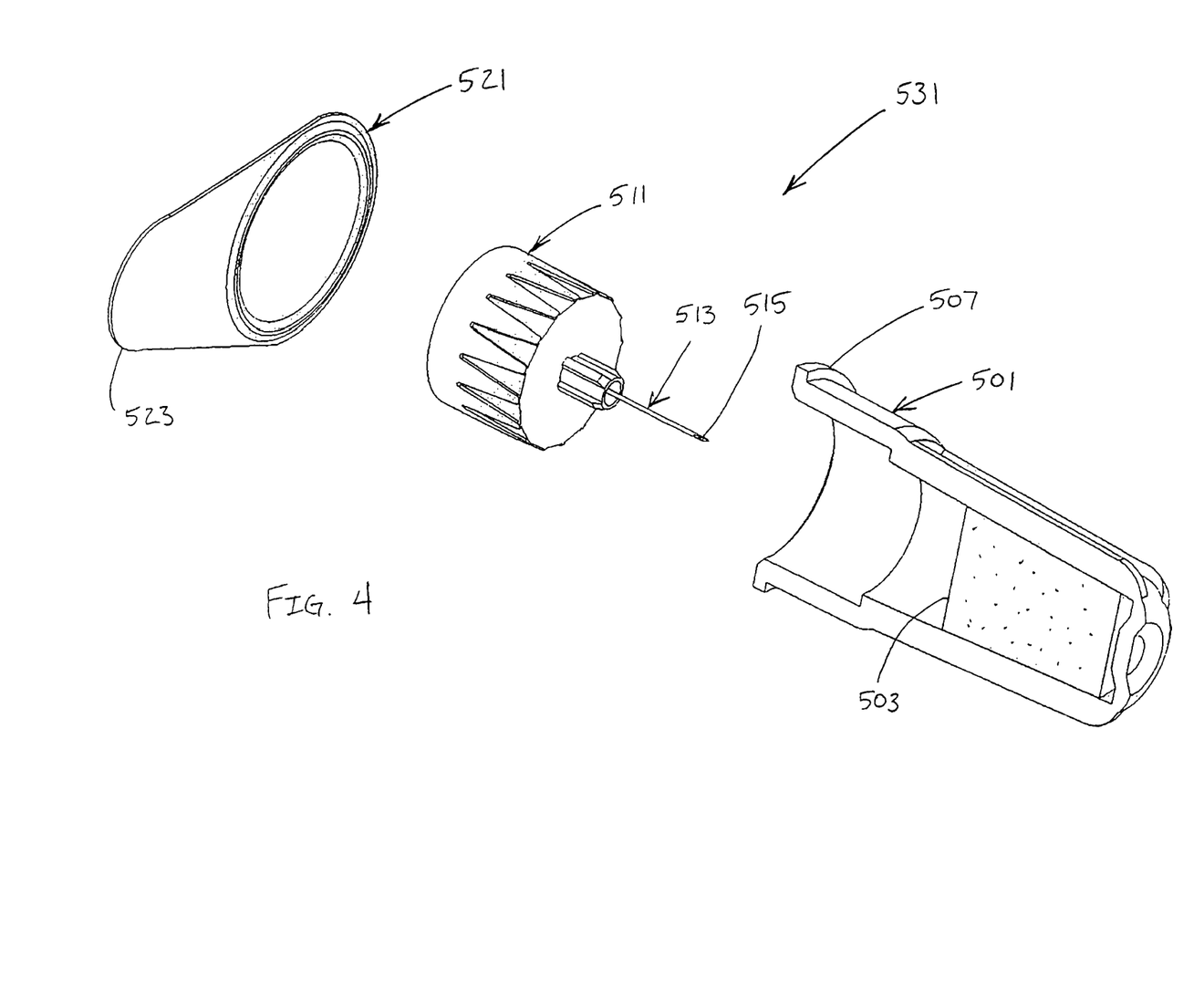
FIG. 4 is an exploded perspective view of an outer cover in partial cross section, a pen needle hub and a seal according to an exemplary embodiment of the present invention in which a needle of the pen needle is disposed in a lubricant reservoir.
Figure 5:
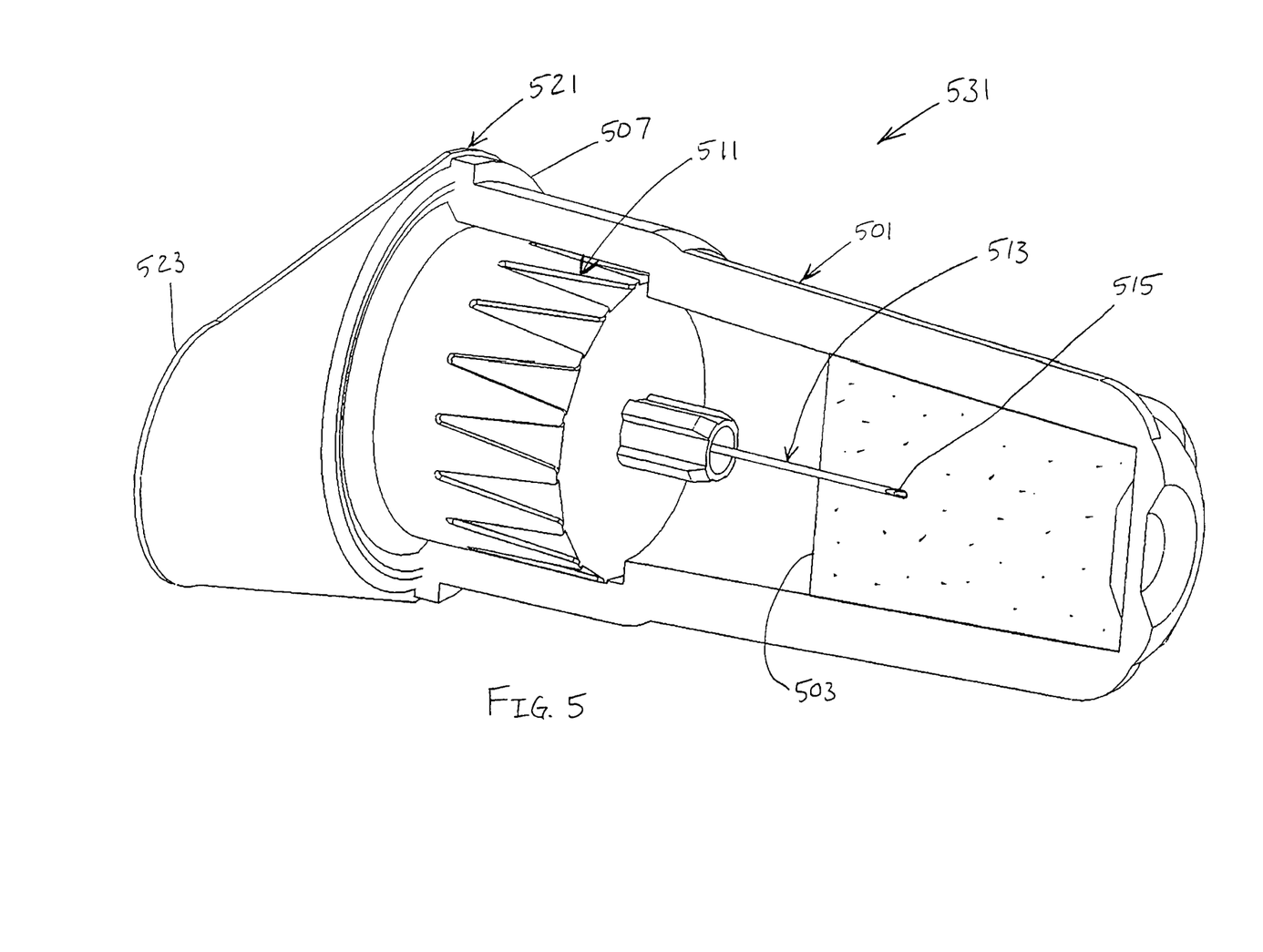
FIG. 5 is a perspective view in partial cross section of the hub disposed in the outer cover of the pen needle of FIG. 4.

In an exemplary embodiment of the present invention shown in FIGS. 4 and 5, a pen needle 531 includes an outer cover 501 connected to a pen needle hub 511, such as by a friction fit. A label or seal 521 is adhered to the outer cover 501 to seal the hub 511 within the outer cover. The label 521 is a sterile barrier for the pen needle 531.

The label 521 is adhered to a first end 507 of the outer cover 501. A lubricant reservoir 503 is disposed within the outer cover 501 such that the patient end 515 of a needle 513 of the hub 511 is disposed within the lubricant reservoir 503 when the hub is disposed in the outer cover, as shown in FIG. 5. The label 521 has an outwardly extending tab 523 to facilitate removal of the label from the outer cover 501.

After the label 521 has been removed and the needle 513 used for an injection, the outer cover 501 may be disposed over the pen needle 531 to shield the needle until the needle is used for a subsequent injection. As shown in FIG. 5, the patient end 515 of the needle 513 is disposed within the lubricant reservoir 503 to facilitate multiple injections with the same needle.

The lubricant reservoir 503 may be a solid or semi-solid matrix, such as a sponge, polymer, gel or other suitable material, impregnated with the lubricant. As shown in FIG. 5, the patient end 515 of the needle 513 is disposed within the lubricant reservoir 503 when the outer cover 501 is on the hub 511. Accordingly, the patient end 515 of the needle 513 is lubricated substantially immediately prior to use by being withdrawn from the lubricant reservoir 503.

Figure 6:
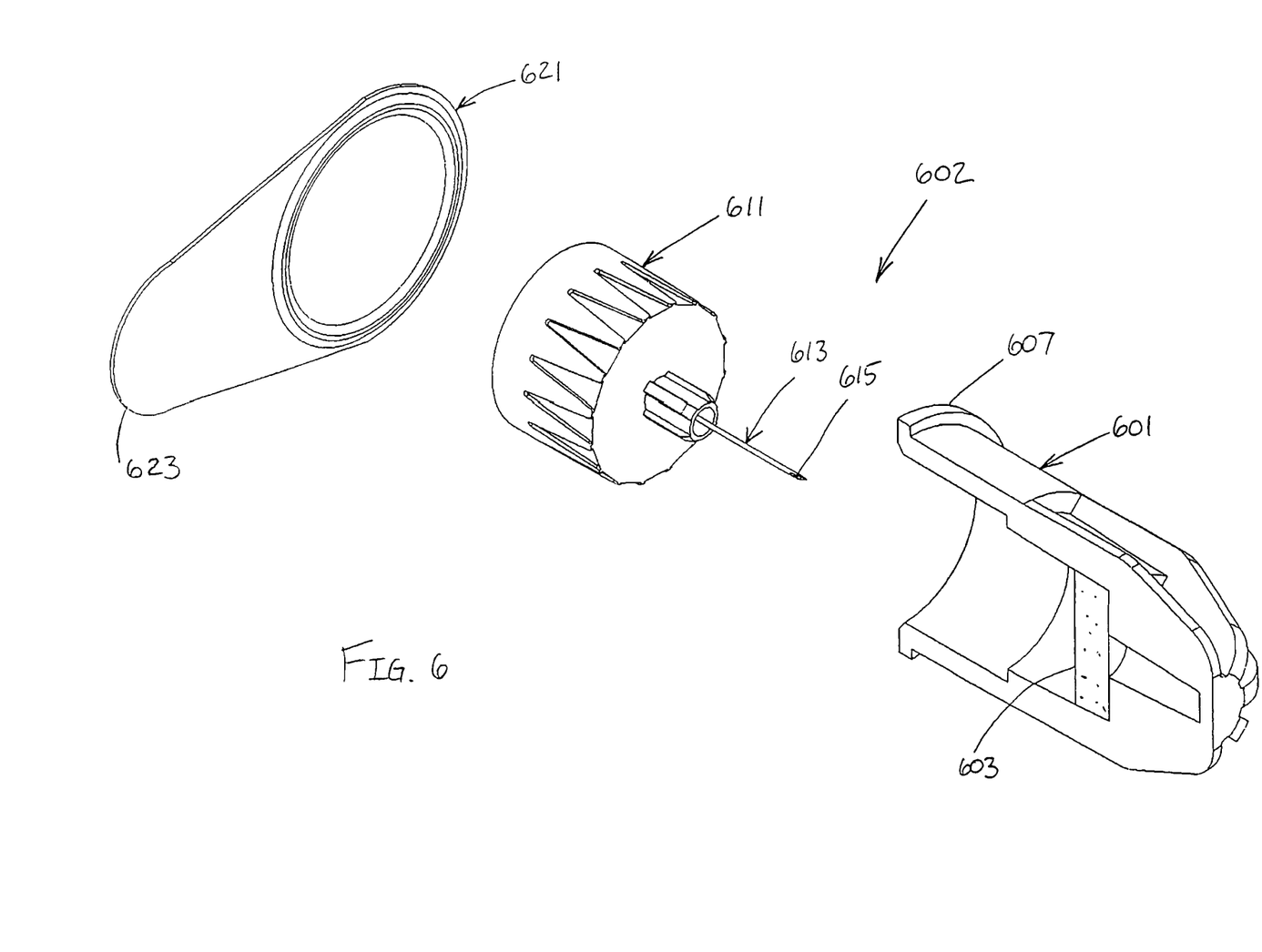
FIG. 6 is an exploded perspective view of an outer cover in partial cross section, a pen needle and a seal according to another exemplary embodiment of the present invention in which a needle passes through a lubricant reservoir in the outer cover.
Figure 7:
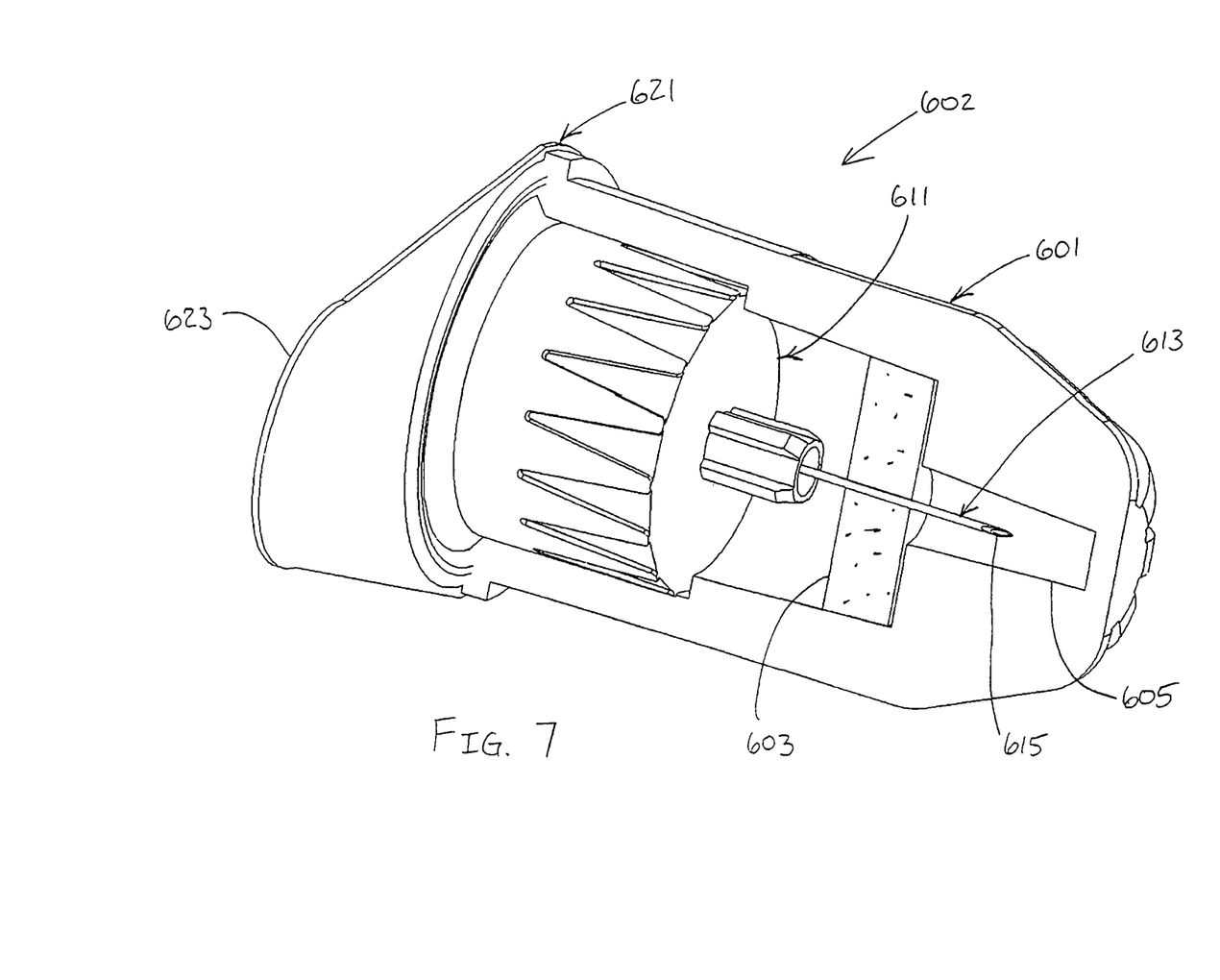
FIG. 7 is a perspective view in partial cross section of the pen needle disposed in the outer cover of FIG. 6.

In another exemplary embodiment of the present invention shown in FIGS. 6 and 7, an outer cover 601 is connected to a hub 611 of a pen needle 602, such as by a friction fit. A label or seal 621 is adhered to the outer cover 601 to seal the hub 611 within the outer cover 601. The label 621 is a sterile barrier for the pen needle 611.

The label 621 is adhered to a first end 607 of the outer cover 601. A lubricant reservoir 603 is disposed within the outer cover 601 such that the patient end 615 of a needle 613 of the pen needle 602 passes through the lubricant reservoir when the pen needle is disposed in the outer cover, as shown in FIG. 7. The label 621 has an outwardly extending tab 623 to facilitate removal of the label from the outer cover 601.

After the label 621 has been removed and the needle 613 used for an injection, the outer cover 601 may be disposed over the pen hub 611 to shield the needle until the needle is used for a subsequent injection. As shown in FIG. 7, the patient end 615 of the needle 613 is not disposed within the lubricant reservoir 603 when the outer cover 601 is reconnected to the hub 611 after a first injection is made. The patient end 615 of the needle 613 is disposed within a chamber 605 of the outer cover 601 that does not contain lubricant. Thus, the patient end 615 of the needle 613 passes through the lubricant reservoir 603 to facilitate multiple injections with the same needle when the outer cover is connected to and removed from the hub 611.

The lubricant reservoir 603 may be a solid or semi-solid matrix, such as a sponge, polymer, gel or other suitable material, impregnated with the lubricant. As shown in FIG. 7, the patient end 615 of the needle 613 is not disposed within the lubricant reservoir 603 when the outer cover 601 is on the pen needle 611, thereby substantially preventing fluid communication between the lubricant reservoir and the medication in the drug delivery pen. Accordingly, the patient end 615 of the needle 613 is lubricated substantially immediately prior to use by being withdrawn through the lubricant reservoir 603.

Figure 8:
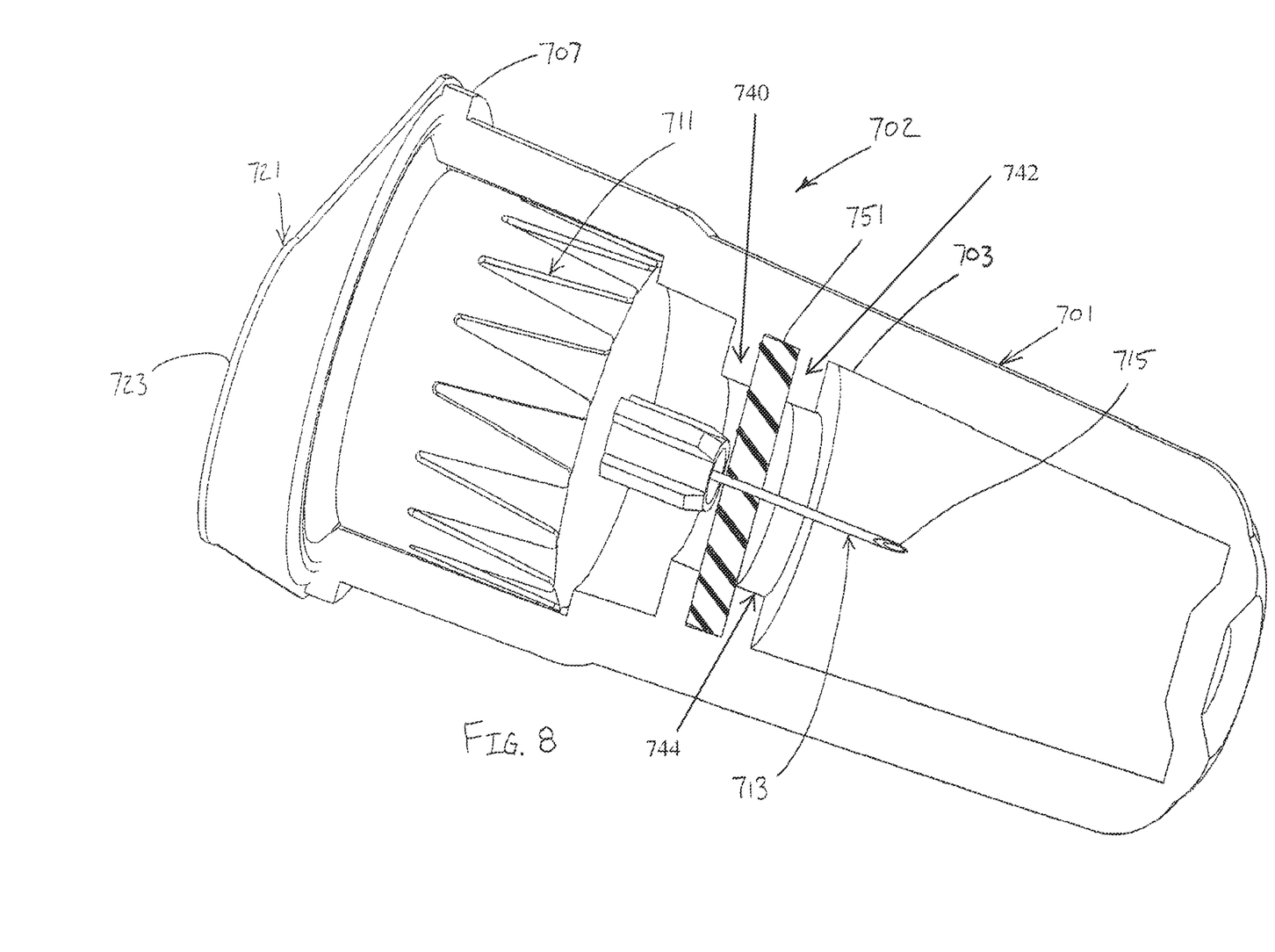
FIG. 8 is a perspective view in partial cross section of an outer cover in partial cross section, a pen needle and a seal according to another exemplary embodiment in which a septum encloses a lubricant reservoir in the outer cover.

In another exemplary embodiment of the present invention, as shown in FIG. 8, an outer cover 701 is connected to a hub 711 of a pen needle 702, such as by a friction fit. A label or seal 721 is adhered to the outer cover 701 to seal the pen hub 711 within the outer cover 701. The label 721 is a sterile barrier for the pen hub 711.

The label 721 is adhered to a first end 707 of the outer cover 701. A lubricant reservoir 703 (shown empty but typically filled partially or entirely with a liquid lubricant) is disposed within the outer cover 701 such that the patient end 715 of a needle 713 of the hub 711 passes through the lubricant reservoir when the hub is disposed in the outer cover, as shown in FIG. 8. A septum 751 is disposed within the outer cover 701 to enclose the lubricant reservoir 703. Specifically, the septum 751 is secured between a first transverse wall 740 and a second transverse wall 742 of the outer cover 701 to prevent axial movement of the septum 751. An inner diameter 744 extends through the first and second transverse walls 740, 742 to allow the needle 713 of the hub 711 to pass through the lubricant reservoir 703. The label 721 has an outwardly extending tab 723 to facilitate removal of the label from the outer cover 701.

After the label 721 has been removed and the needle 713 used for an injection, the outer cover 701 may be disposed over the hub 711 to shield the needle until the needle is used for a subsequent injection. As shown in FIG. 8, the patient end 715 of the needle 713 is disposed within the lubricant reservoir 703 when the outer cover 701 is reconnected to the hub 711 after a first injection is made. Accordingly, the patient end 715 of the needle 713 is disposed within the lubricant reservoir 703 to facilitate multiple injections with the same needle.

The lubricant reservoir 703 may contain a liquid lubricant or a solid or semi-solid matrix, such as a sponge, polymer, gel or other suitable material, impregnated with the lubricant. As shown in FIG. 8, the patient end 715 of the needle 713 is disposed within the lubricant reservoir 703 when the outer cover 701 is on the pen needle 702. Accordingly, the patient end 715 of the needle 713 is lubricated substantially immediately prior to use by being withdrawn from the lubricant reservoir 703. The patient end 715 of the needle 713 penetrates the septum 751 when the outer cover 701 is connected to and removed from the pen needle 702.

As shown in FIGS. 4-8, an inner shield is not used to cover the patient end of the needle inside the outer cover.

The lubricant may be an antimicrobial solution. Preferably, the lubricant solution contains a lubricant, such as siloxanes, which includes functionalized siloxanes. Preferably, the lubricant solution contains solvents, such as water/surfactant mixtures, alcohols, alkanes, 1,2-trans-dichloroethylene or other solvents for silicones. Preferably, the lubricant solution contains antimicrobial agents, such as meta-cresol. A commercial manufacturer of a medical-grade silicone for lubrication is Dow Corning, and a suitable lubricant is Dow Corning 360 fluid (a trimethyl-terminated polydimethylsiloxane), which is available in 100 cS, 350 cS and 12,500 cS viscosities. Preferably, the lubricant is a trimethyl-terminated PDMS having a viscosity of 100 cS.

The needle may be heat-treated for greater hardness, or made of an alloy harder than 304 stainless steel. The point geometry of the needle may be altered to maintain sharpness of the needle over multiple injections. The needle may be treated with an adhesion promoter to improve durability of the lubricant coating. The adhesion promoter may include vapor-deposited polymers, such as poly(para-xylene), aqueous or solvent-based silanes, aminosilicones, and mechanical roughening of the needle surface.

A pen needle according to the exemplary embodiments of the present invention may include an automatic disabling device that prevents the needle from being used more than a predetermined number of times. One use is defined as one cycle of removing and inserting the needle in the outer cover. The outer cover may be sized to be received within the pen cap of a commercial drug delivery pen (FIGS. 1 and 2). A reusable lid (instead of the label) may be disposed over the non-patient end of the needle when the needle is not being used and is stored in the outer cover.

The lubricity and durability of a lubricant coating generally compete against each other. A less durable lubricant produces lower penetration forces, but penetration forces increase rapidly after the first use. A more durable lubricant results in less performance degradation as the needle is reused, but penetration forces are generally higher from the first use. Performance may be improved by treating a needle with a low-viscosity lubricant immediately before penetration. However, if the needle to be lubricated is treated a long time before use, the lubricant may migrate away from the needle, thereby reducing the performance thereof.

Figure 9:
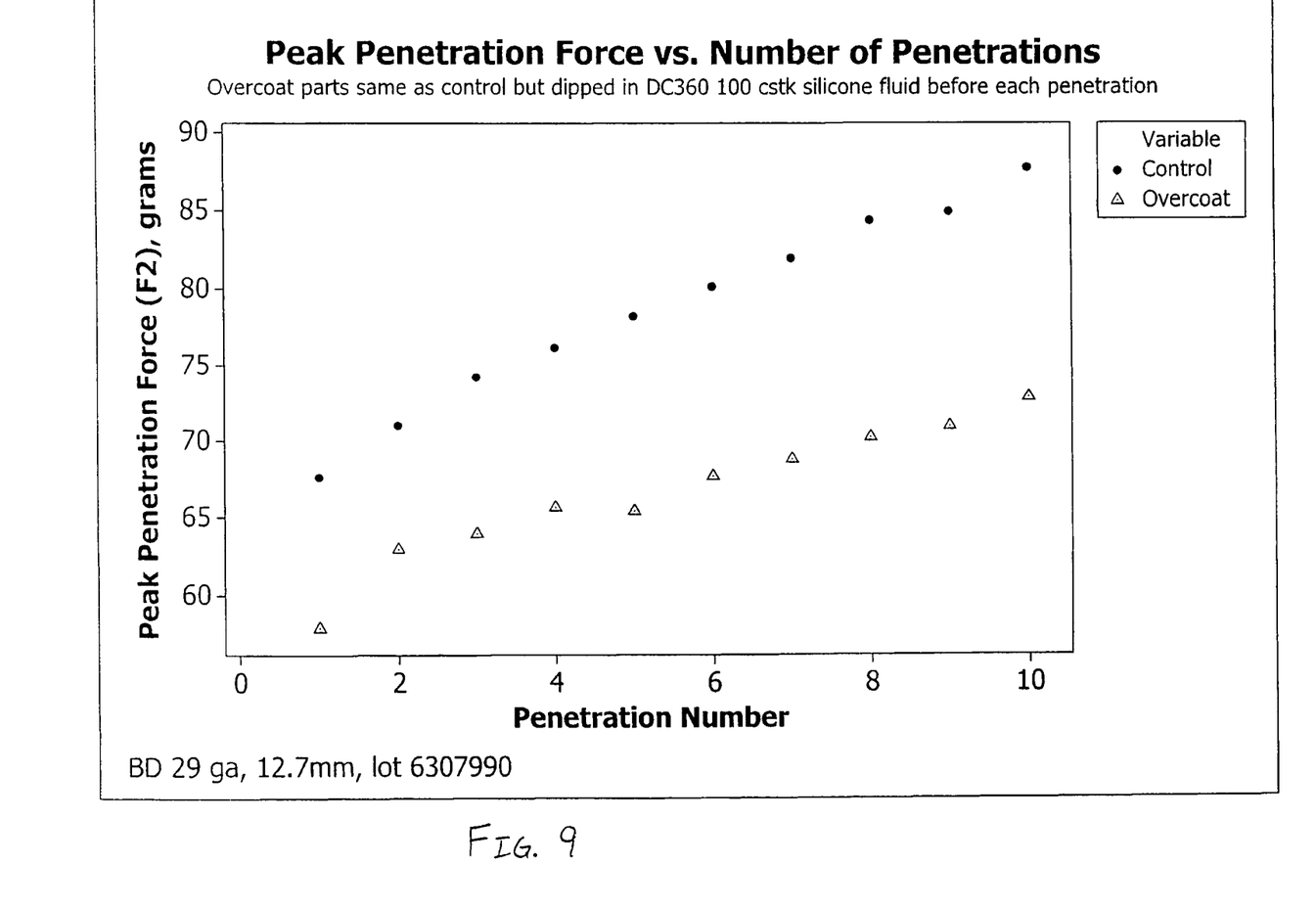
FIG. 9 is a graph of peak penetration force vs. the number of penetrations.

FIG. 9 is a plot of peak penetration force as a function of multiple penetrations with the same needle. Each data point is an average of five (5) observations. The control samples are Becton Dickinson 29 gauge, 12.7 mm pen needles produced under Lot 6307990, and were penetrated into white insulin vial stoppers. The overcoat samples were the same as the control samples, but were dipped in a trimethyl-terminated polydimethylsiloxane fluid (100 Cs viscosity) immediately before each penetration test. A new vial stopper was used for each penetration. Thus, as shown in FIG. 9, overcoating a conventionally lubricated needle with a low viscosity lubricant reduces peak penetration forces by approximately 20 percent. The average penetration force after ten (10) penetrations was 71 g for the overcoated samples, compared to 88 g for the conventionally lubricated sample. The average penetration force for the conventional (control) needles was 67 g during the first use. Accordingly, the overcoated needle has a similar performance after ten (10) penetrations as the first use of a conventionally lubricated needle.

The foregoing embodiments and advantages are merely exemplary and are not to be construed as limiting the scope of the present invention. The description of exemplary embodiments of the present invention is intended to be illustrative, and not to limit the scope of the present invention. Various modifications, alternatives and variations will be apparent to those of ordinary skill in the art, and are intended to fall within the scope of the invention as defined in the appended claims and their equivalents.

The invention claimed is:

1. A pen needle assembly, comprising:
an injection pen including a removable pen cap and a medicament reservoir; and
a pen needle configured to engage the injection pen when the pen cap is removed, the pen needle including:
a hub having a protruding portion, and an engagement portion for engaging the injection pen, the engagement portion having an interior and an open proximal end;
a needle fixedly connected to said protruding portion of said hub, said needle having a patient end, formed for insertion into a patient, and a proximal end extending into said interior of said engagement portion of said hub for communicating with said medicament reservoir;
a reusable outer cover for repeatedly receiving said engagement portion of said hub and said needle between multiple injections of the pen needle, the reusable outer cover including a first transverse wall, a second transverse wall, and an inner diameter of the first and second transverse walls extending through the first and second transverse walls, the first and second transverse walls each including a ring structure extending radially inwardly from an inner diameter of the reusable outer cover;

a septum secured between the first and second transverse walls of the reusable outer cover to prevent axial movement of the septum; and a lubricant reservoir disposed in said outer cover such that at least a portion of said needle passes through the septum and is disposed in said lubricant reservoir whenever said engagement portion of said hub and said needle are received by said outer cover; wherein said reusable outer cover is sized to be received within said pen cap.

2. The pen needle assembly according to claim 1, wherein a seal is removably connected to said outer cover.

3. The pen needle assembly according to claim 2, wherein said hub is received by said outer cover when said seal is connected to said outer cover.

4. The pen needle assembly according to claim 1, wherein said lubricant reservoir comprises an antimicrobial solution.

5. The pen needle assembly according to claim 1, wherein said lubricant reservoir comprises solvents.

6. The pen needle assembly according to claim 1, wherein said lubricant reservoir comprises a lubricant impregnated matrix.

7. The pen needle assembly according to claim 1, wherein said patient end of said needle is disposed in said lubricant reservoir when said outer cover receives said hub.

8. The pen needle assembly according to claim 1, wherein said patient end of said needle is not disposed in said lubricant reservoir when said outer cover receives said hub.

9. The pen needle assembly according to claim 8, wherein said lubricant reservoir is disposed between said hub and said patient end of said needle.

10. The pen needle assembly according to claim 1, wherein the needle is substantially uncovered prior to connecting the hub and the outer cover in order for the lubricant reservoir to lubricate the needle when connected.

11. The pen needle assembly according to claim 1, further comprising a recess between the first and second transverse walls; wherein the septum is disposed in the recess and adjacent to each of the first and second transverse walls; and an inner diameter of the recess corresponds to an outer diameter of the septum.

12. The pen needle assembly according to claim 1, wherein said lubricant reservoir comprises a liquid lubricant.

13. The pen needle assembly according to claim 1, wherein said septum is disposed between said hub and said patient end of said needle; and the septum includes a smooth circumferential outer diameter that engages the reusable outer cover.

14. The pen needle assembly according to claim 13, wherein said patient end of said needle is disposed in said lubricant reservoir when said outer cover receives said hub.

15. The pen needle assembly according to claim 1, wherein said needle is treated with an adhesion promoter.

16. A method of injecting a medicament using a pen needle, comprising the steps of:

lubricating a patient end of a needle with a lubricant in a lubricant reservoir disposed in a reusable outer cover, the reusable outer cover including a first transverse wall, a first inner diameter distal to the first transverse wall, a second transverse wall, a second inner diameter proximal to the second transverse wall, inner diameters of the first and second transverse walls extending through the first and second transverse walls, a septum secured between the first and second transverse walls to prevent axial movement of the septum, and a third inner diameter that engages the septum, wherein the first, second and third inner diameters are of a same size;

connecting an engagement portion of a hub of the pen needle to an injection pen, the injection pen including a removable pen cap and a medicament reservoir;

injecting the medicament through the needle into an injection site; and repeating the lubricating step with the same needle between multiple injections, such that when lubricating the patient end of the needle, the reusable outer cover repeatedly receives the needle and the engagement portion of the hub, said engagement portion of the hub having an interior and an open proximal end, said needle being fixedly connected to a protruding portion of said hub and having a proximal end extending into said interior of said engagement portion of the hub for communicating with said medicament reservoir; wherein said reusable outer cover is sized to be received within said pen cap.

17. The method of injecting the medicament according to claim 16, further comprising passing said patient end of the needle through said lubricant reservoir to lubricate the needle prior to the injecting step.

18. The method of injecting the medicament according to claim 16, further comprising storing said patient end of the needle in said lubricant reservoir to lubricate the needle prior to the injecting step.

19. The method of injecting the medicament according to claim 18, further comprising passing the patient end of the needle through the septum after the patient end of the needle is removed from the lubricant reservoir.

20. The method of injecting the medicament according to claim 18, further comprising passing the patient end of the needle through the septum before storing the patient end of the needle in the lubricant reservoir.

21. The method of injecting the medicament according to claim 16, further comprising passing said patient end of the needle through said lubricant reservoir after the injecting step.

22. A method of injecting a medicament using a pen needle, comprising the steps of:

disposing a patient end of a needle fixed to a protruding portion of a hub and an engagement portion of the hub in a reusable outer cover, the reusable outer cover including a first transverse wall, a second transverse wall, inner diameters of the first and second transverse walls extending through the first and second transverse walls, the first and second transverse walls each including a ring structure extending radially inwardly from an inner diameter of the reusable outer cover, and a septum secured between the first and second transverse walls of the reusable outer cover to prevent axial movement of the septum;

lubricating the patient end of the needle with a lubricant disposed in the reusable outer cover;
connecting the engagement portion of the hub of the pen needle to an injection pen, the injection pen including a removable pen cap and a medicament reservoir;
removing the needle and the hub from the reusable outer cover;
injecting the medicament through the needle;
after the injecting step, disposing the patient end of the needle and the engagement portion of the hub in the reusable outer cover, lubricating the patient end of the needle with the lubricant disposed in the reusable outer cover, and removing the needle and the hub from the reusable outer cover; and
injecting the medicament through the needle a second time; wherein said reusable outer cover is sized to be received within said pen cap.

* * * * *